(12) United States Patent
Scheuermann et al.

(10) Patent No.: US 7,101,391 B2
(45) Date of Patent: Sep. 5, 2006

(54) PRIMARILY NIOBIUM STENT

(75) Inventors: Torsten Scheuermann, Munich (DE); Eckhard Alt, Ottobrunn (DE)

(73) Assignee: Inflow Dynamics Inc., Springfield, VA (US)

( * ) Notice: Subject to any disclaimer, the term of this patent is extended or adjusted under 35 U.S.C. 154(b) by 692 days.

(21) Appl. No.: 10/232,774

(22) Filed: Aug. 31, 2002

(65) Prior Publication Data

US 2003/0088308 A1 May 8, 2003

Related U.S. Application Data

(63) Continuation-in-part of application No. 09/663,896, filed on Sep. 18, 2000, now Pat. No. 6,478,815.

(51) Int. Cl.
*A61F 2/06* (2006.01)
(52) U.S. Cl. .................................... 623/1.15
(58) Field of Classification Search ................ 606/108, 606/191, 194, 198, 195; 623/1.11–1.15, 623/1.16–1.22, 1.44, 1.45, 1.27, 1.32
See application file for complete search history.

(56) References Cited

U.S. PATENT DOCUMENTS

| | | |
|---|---|---|
| 3,346,379 A | 10/1967 | Rhodin |
| 4,778,461 A | 10/1988 | Pietsch et al. |
| 5,496,359 A | 3/1996 | Davidson |
| 5,588,443 A | 12/1996 | Davidson |
| 5,607,463 A | 3/1997 | Schwartz et al. |
| 5,628,787 A | 5/1997 | Mayer |
| 5,630,840 A | 5/1997 | Mayer |
| 5,643,794 A | 7/1997 | Liu et al. |
| 5,647,858 A | 7/1997 | Davidson |
| 5,653,691 A | 8/1997 | Rupp et al. |
| 5,679,470 A | 10/1997 | Mayer |
| 5,693,066 A | 12/1997 | Rupp et al. |
| 5,716,981 A | 2/1998 | Hunter et al. |
| 5,749,919 A | 5/1998 | Blanc |
| 5,758,562 A | 6/1998 | Thompson |
| 5,759,474 A | 6/1998 | Rupp et al. |
| 5,772,864 A | 6/1998 | Moller et al. |
| 5,800,511 A | 9/1998 | Mayer |
| 5,810,871 A | 9/1998 | Tuckey et al. |
| 5,824,077 A | 10/1998 | Mayer |
| 5,843,168 A | 12/1998 | Dang |
| 5,851,222 A | 12/1998 | Taylor et al. |
| 5,886,026 A | 3/1999 | Hunter et al. |

(Continued)

FOREIGN PATENT DOCUMENTS

EP    0 601 804 A1    6/1994

(Continued)

OTHER PUBLICATIONS

PCT International Search Report, mailed Feb. 5, 2004.

*Primary Examiner*—Vy Bui
(74) *Attorney, Agent, or Firm*—Fish & Richardson P.C.

(57) ABSTRACT

In a process of fabricating a stent composed primarily of niobium alloyed with a trace amount of zirconium, tantalum, or titanium for hardening, the stent is annealed under vacuum in a substantially oxygen-free environment. The vacuum is preferably maintained at pressure less than $10^{-4}$ millibars, oxygen-content less than about 80 parts per million, and the annealing temperature exceeds 400° C. for at least one hour, and is preferably kept in a range from about 1100–1200° C. for several hours. This may be followed by applying a surface layer of oxide, such as iridium oxide, with a thickness of 299–300 nm to the stent.

6 Claims, 1 Drawing Sheet

U.S. PATENT DOCUMENTS

| | | |
|---|---|---|
| 5,888,201 A | 3/1999 | Stinson et al. |
| 5,899,934 A | 5/1999 | Amundson et al. |
| 5,913,871 A | 6/1999 | Werneth et al. |
| 5,913,896 A | 6/1999 | Boyle et al. |
| 5,931,867 A | 8/1999 | Hanindl |
| 5,957,974 A | 9/1999 | Thompson et al. |
| 5,994,341 A | 11/1999 | Hunter et al. |
| 6,013,854 A | 1/2000 | Moriuchi |
| 6,019,786 A | 2/2000 | Thompson |
| 6,056,906 A | 5/2000 | Werneth et al. |
| 6,068,623 A | 5/2000 | Zadno-Azizi et al. |
| 6,099,561 A | 8/2000 | Alt |
| 6,106,530 A | 8/2000 | Harada |
| 6,110,204 A | 8/2000 | Lazarov et al. |
| 6,124,779 A | 9/2000 | Yamamoto |
| 6,136,023 A | 10/2000 | Boyle |
| 6,156,064 A | 12/2000 | Chouinard |
| 6,174,316 B1 | 1/2001 | Tuckey et al. |
| 6,183,508 B1 | 2/2001 | Stinson et al. |
| 6,187,037 B1 | 2/2001 | Satz |
| 6,200,256 B1 | 3/2001 | Weinberger |
| 6,200,685 B1 | 3/2001 | Davidson |
| 6,203,732 B1 | 3/2001 | Clubb et al. |
| 6,210,312 B1 | 4/2001 | Nagy |
| 6,210,437 B1 | 4/2001 | Frautschi |
| 6,217,503 B1 | 4/2001 | Weinberger et al. |
| 6,238,491 B1 | 5/2001 | Davidson et al. |
| 6,251,135 B1 | 6/2001 | Stinson et al. |
| 6,264,688 B1 | 7/2001 | Herklotz et al. |
| 6,287,332 B1 | 9/2001 | Bolz et al. |
| 6,340,367 B1 | 1/2002 | Stinson et al. |
| 6,340,368 B1 | 1/2002 | Verbeck |
| 6,342,068 B1 | 1/2002 | Thompson |
| 6,375,628 B1 | 4/2002 | Zadno-Azizi et al. |
| 6,379,380 B1 | 4/2002 | Satz |
| 6,383,217 B1 | 5/2002 | Satz |
| 6,387,121 B1 | 5/2002 | Alt |
| 6,394,945 B1 | 5/2002 | Chan et al. |
| 6,402,859 B1 | 6/2002 | Ishii et al. |
| 6,447,550 B1 | 9/2002 | Hunter et al. |
| 6,451,052 B1 | 9/2002 | Burmeister et al. |
| 6,468,219 B1 | 10/2002 | Njemanze |
| 6,478,815 B1 | 11/2002 | Alt |
| 6,485,507 B1 | 11/2002 | Walak et al. |
| 6,500,203 B1 | 12/2002 | Thompson et al. |
| 6,503,272 B1 | 1/2003 | Duerig et al. |
| 6,506,411 B1 | 1/2003 | Hunter et al. |
| 6,509,094 B1 | 1/2003 | Shah et al. |
| 6,527,802 B1 | 3/2003 | Mayer |
| 6,527,938 B1 | 3/2003 | Bales et al. |
| 6,530,947 B1 | 3/2003 | Euteneuer et al. |
| 6,537,310 B1 | 3/2003 | Palmaz et al. |
| 6,549,951 B1 | 4/2003 | Hui et al. |
| 2001/0001317 A1 | 5/2001 | Duerig et al. |
| 2001/0032013 A1 | 10/2001 | Marton |
| 2002/0042645 A1 | 4/2002 | Shannon |
| 2002/0138133 A1 | 9/2002 | Lenz et al. |
| 2002/0165600 A1 | 11/2002 | Banas et al. |

FOREIGN PATENT DOCUMENTS

| | | |
|---|---|---|
| EP | 0 688 545 A1 | 12/1995 |
| EP | 0 810 889 B1 | 2/1996 |
| EP | 0 788 802 A2 | 8/1997 |
| EP | 0 799 607 A2 | 10/1997 |
| EP | 0 803 233 A2 | 10/1997 |
| EP | 0 804 909 A2 | 11/1997 |
| EP | 0 855 171 A2 | 7/1998 |
| EP | 0 873 734 A | 10/1998 |
| EP | 0 884 029 A1 | 12/1998 |
| EP | 0 890 346 A1 | 1/1999 |
| EP | 1 046 722 A1 | 10/2000 |
| EP | 1 254 673 A1 | 6/2002 |
| EP | 1 222 901 A2 | 7/2002 |
| EP | 1 247 537 A1 | 10/2002 |
| EP | 0 854 693 B1 | 11/2002 |
| EP | 1 281 374 A2 | 2/2003 |
| WO | WO 94/16646 | 8/1994 |
| WO | WO 95/11055 | 4/1995 |
| WO | WO 95/18585 | 7/1995 |
| WO | WO 95/27092 | 10/1995 |
| WO | WO 95/30384 | 11/1995 |
| WO | WO 95/31945 | 11/1995 |
| WO | WO 96/24860 | 8/1996 |
| WO | WO 96/25960 | 8/1996 |
| WO | WO 96/38594 | 12/1996 |
| WO | WO 97/07740 | 3/1997 |
| WO | WO 97/13475 | 4/1997 |
| WO | WO 97/19723 | 6/1997 |
| WO | WO 97/45105 | 12/1997 |
| WO | WO 98/42390 | 10/1998 |
| WO | WO 98/43550 | 10/1998 |
| WO | WO 98/48732 | 11/1998 |
| WO | WO 99/47076 | 9/1999 |
| WO | WO 99/45161 | 10/1999 |
| WO | WO 99/51299 | 10/1999 |
| WO | WO 99/58184 | 11/1999 |
| WO | WO 99/62624 | 12/1999 |
| WO | WO 00/54836 A1 | 9/2000 |
| WO | WO 00/61203 | 10/2000 |
| WO | WO 00/64506 | 11/2000 |
| WO | WO 00/68448 | 11/2000 |
| WO | WO 00/69359 | 11/2000 |
| WO | WO 00/72893 A2 | 12/2000 |
| WO | WO 00/78394 A1 | 12/2000 |
| WO | WO 00/78395 A1 | 12/2000 |
| WO | WO 01/08600 A2 | 2/2001 |
| WO | WO 01/21229 A1 | 3/2001 |
| WO | WO 01/35865 A1 | 5/2001 |
| WO | WO 01/41826 A1 | 6/2001 |
| WO | WO 01/55473 A1 | 8/2001 |
| WO | WO 01/553473 A1 | 8/2001 |
| WO | WO 01/72349 A1 | 10/2001 |
| WO | WO 02/05863 A1 | 1/2002 |
| WO | WO 02/26271 A1 | 4/2002 |
| WO | WO 02/26281 A1 | 4/2002 |
| WO | WO 02/28458 A1 | 4/2002 |
| WO | WO 02/30271 A2 | 4/2002 |
| WO | WO 02/38080 A2 | 5/2002 |
| WO | WO 02/43787 A1 | 6/2002 |
| WO | WO 02/060506 A1 | 8/2002 |
| WO | WO 02/076349 A1 | 10/2002 |
| WO | WO 02/078762 A1 | 10/2002 |
| WO | WO 02/080815 A2 | 10/2002 |
| WO | WO 02/087473 A1 | 11/2002 |
| WO | WO 03/003943 A2 | 1/2003 |
| WO | WO 03/008657 A1 | 1/2003 |
| WO | WO 03/01337 A1 | 2/2003 |
| WO | WO 03/015662 A1 | 2/2003 |

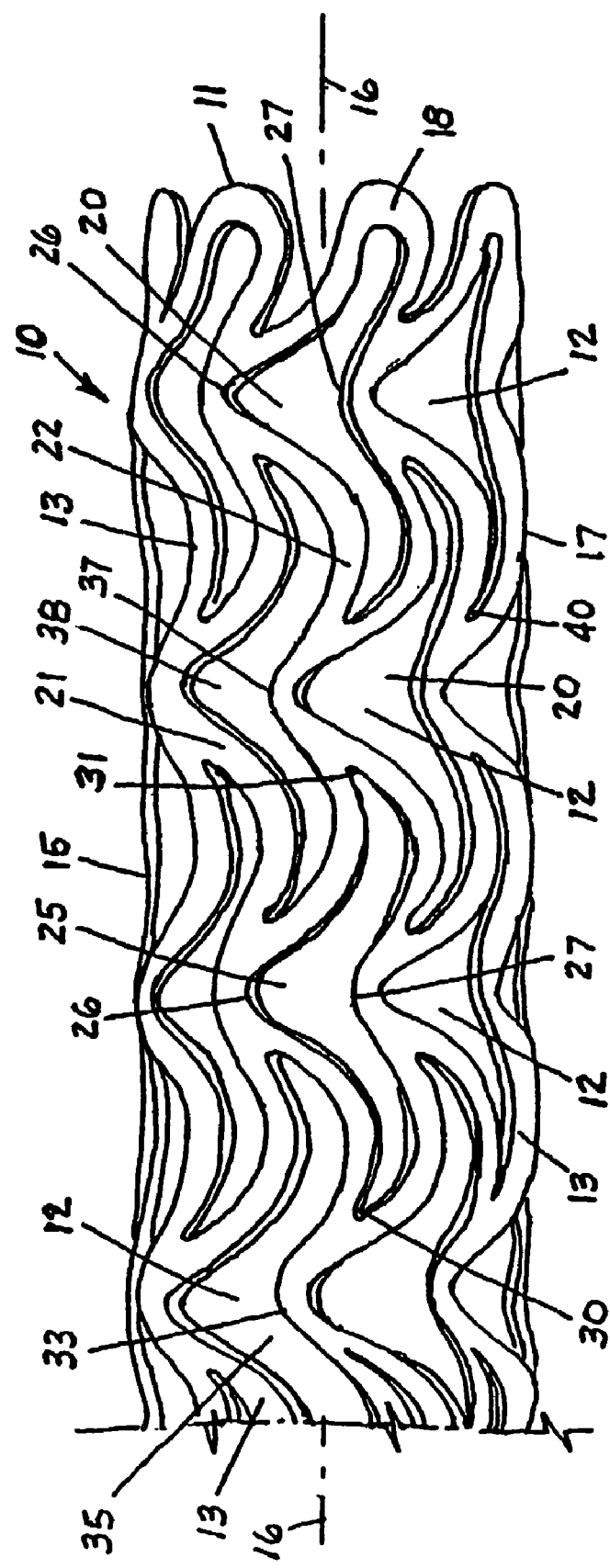

PRIMARILY NIOBIUM STENT

CROSS-REFERENCE TO RELATED APPLICATIONS

This application is a continuation-in-part of U.S. patent application Ser. No. 09/663,896, filed Sep. 18, 2000 ("the '896 application") now issued as U.S. Pat. No. 6,478,815, and is further related to U.S. patent application Ser. No. 09/634,667 now issued as U.S. Pat. No. 6,387,121, filed Aug. 8, 2000 ("the '667 application"), both of the same assignee as the present application.

BACKGROUND OF THE INVENTION

The present invention relates generally to stents that are implantable or deployable in a vessel or duct within the body of a patient to maintain the lumen of the duct or vessel open, and more particularly to improvements in stent structures.

When inserted and deployed in a vessel, duct or tract of the body, for example a coronary artery after dilatation of the artery by balloon angioplasty, a stent acts as a prosthesis to maintain the vessel, duct or tract (generally referred to as a vessel for convenience herein) open. The stent has the form of an open-ended tubular element with openings through its sidewall to enable its expansion from a first outside diameter which is sufficiently small to allow it to be navigated through the vessel to a target site where it is to be deployed, to a deployed second outside diameter sufficiently large to engage the inner lining of the vessel for retention at the target site.

An occluded coronary artery, for example, is typically attributable to a buildup of fatty deposits or plaque on the inner lining of the vessel. A balloon angioplasty procedure is the treatment of choice to compress the deposits against the inner lining of the vessel to open the lumen. Alternatively, removal of plaque may be achieved by laser angioplasty, or by rotationally cutting the material into finely divided particles which are dispersed in the blood stream. For a large segment of patients undergoing the procedure, traditional angioplasty has resulted in new blockage of the treated vessel only a relatively short time thereafter, attributable to trauma to the blood vessel wall from the original procedure. The mechanism responsible for this restenosis or re-occlusion of the vessel lumen is intimal hyperplasia, a rapid proliferation of smooth muscle cells in the affected region of the wall.

To maintain the vessel open, it has become customary to install a stent at the trauma site at the time of or shortly after the angioplasty procedure is performed. The stent is deployed by radial expansion under outwardly directed radial pressure exerted, for example, by active inflation of a balloon of a balloon catheter on which the stent is mounted. In some instances, passive spring characteristics of a preformed elastic (i.e., self-opening) stent serves the purpose. The stent is thus expanded to engage the inner lining or inwardly facing surface of the vessel wall with sufficient resilience to allow some contraction but also with sufficient stiffness to largely resist the natural recoil of the vessel wall.

The presence of the stent in the vessel, however, tends to promote thrombus formation as blood flows through the vessel, which results in an acute blockage. The thrombosis and clotting may be reduced or even eliminated by appropriate surface characteristics of the stent, sufficient to achieve this purpose. At the outward facing surface of the stent in contact or engagement with the inner lining of the vessel, tissue irritation can exacerbate restenosis attributable to hyperplasia.

Another factor affecting the choice of the stent and the stent material is allergic reaction to common stent materials suffered by a statistically significant percentage of the patient population subjected to stenting. These materials include chrome, nickel, and medical grade 316L stainless steel, which contains about 16% nickel. For such patients, the allergic reaction may be sufficient that stent implant is contraindicated. Wholly biodegradable stents of possibly sufficient radial strength are currently undergoing tests and may prove suitable in such cases.

Another consideration in material selection is the need for the implanting physician to be able to visualize the position of the stent during implantation to the desired target site in the body, and for purposes of examination from time to time thereafter at the implant site, typically by x-ray fluoroscopy. The wall of the stent must be sufficiently thick, depending on the stent material, not only to withstand the vessel wall recoil that invariably follows deployment at the target site, but to allow the stent to be seen on the fluoroscope. Various materials, such as 316L stainless steel, possess suitable mechanical strength. Typical stent wall or wire thicknesses have ranged from 70 to 200 microns (or micrometers, $\mu$m). A 70 to 80 $\mu$m thick 316L steel stent offers sufficient strength to resist recoil so as to maintain a lumen diameter close to the diameter achieved at full deployment by balloon inflation. This relatively thin and tiny metal structure creates little shadow on a fluoroscopic picture, however, since the x-ray absorption of the metal is low. Increasing the wall thickness of the stent to enhance its radiopacity and recoil resistance makes the stent less flexible, however, which adversely affects its maneuverability through narrow vessels and the amount of balloon pressurization necessary to enlarge the stent diameter sufficiently during deployment, with concomitant increased risk of balloon rupture.

It follows that a suitable stent for successful interventional placement should possess features of relatively non-allergenic reaction, good radiopacity, freedom from distortion on magnetic resonance imaging (MRI), flexibility with suitable elasticity to be plastically deformable, resistance to vessel recoil, sufficient thinness to minimize obstruction to flow of blood (or other fluid or material in vessels other than the cardiovascular system), and biocompatibility to avoid of vessel re-occlusion. Selection of the stent material, as well as design of the stent, plays an important role in influencing these features.

Aside from vascular usage, other ducts or tracts of the human body in which a stent might be installed to maintain an open lumen include the tracheo-bronchial system, the biliary hepatic system, the esophageal bowel system, and the urinary tract. Many of the same requirements are found in these other endoluminal usages of stents.

Despite improvements in the design and construction of coronary stents, restenosis remains a problem. A major contributing factor is the inability of the body to incorporate the implanted foreign material quickly. Basic research with cell cultures and animal experiments have demonstrated that the degree of endothelialization of the foreign body determines the amount of the restenosis. It has been an assumption among industry practitioners and researchers that a highly polished and smooth surface is beneficial to prevent stent thrombosis and to facilitate endothelialization, but experiments indicate this may not be entirely true.

A significant reason for the lack of a high clinical success rate with electropolished stents is the fact that the smooth muscle cells which seek to envelop a foreign body, such as a stent strut into the vessel wall, require a higher degree of proliferation to cover the foreign body. The continuing flow of blood with a high pressure and high shearing stress prevents the migration of smooth muscle cells, which proliferate from the media and adventitial cells of a stented vessel such as a coronary artery. It has been shown that a slightly rough surface considerably facilitates the coverage by smooth muscle cells, leading to a functional endothelial layer even after 10 to 14 days after stent implantation. A single layer of endothelial cells has been found to seal the neointima and thereby prevent the stimulus which facilitates and enhances the proliferation of cells beyond mere coverage of the foreign body.

The thinner the stent strut, the less the lumen of the stented vessel is obstructed. Moreover, a thin stent is more easily covered by a neoendothelial build-up. Accordingly, it is desirable to make the stent wall as thin as can be practically achieved. But the fluoroscopic visibility of stainless steel, for example, in a thickness below 60 μm is very poor because of the limited extinction of x-rays by such a thin metal tube.

Some improvement has been achieved by applying a suitable adherent material layer to stent core material of medical grade implantable 316L stainless steel. Layer materials have included gold and certain other noble metals, such as platinum. Such materials typically exhibit much greater radiopacity than stainless steel, that renders the stent highly visible under fluoroscopy as it is being advanced through the vessel lumen to the desired site of deployment, as well as after deployment. They are also substantially non-allergenic and non-thrombogenic. Such coating may be provided in a very thin layer, so the stent wall thickness is determined almost solely by considerations of mechanical strength. Coatings, however, present a need for absolute adherence to the underlying metal of the stent to avoid cracking or defects in the homogeneous overlying layer, and sufficient resistance to peeling or flaking of the layer during insertion, and especially during expansion of the diameter of the stent as it is being deployed in final position in the artery at the target site, objectives which are not easily achievable.

The disadvantage of reduced mechanical strength of noble metals such as gold or platinum—which makes them unsuitable if sought to be used alone for application in the human vascular system—is overcome by the use of a core composed of a material such as stainless steel, having considerably better mechanical properties than the noble metal. But the presence of cracks or related defects in the surface coating can produce a galvanic potential which could ultimately lead to corrosion of the underlying steel or lesser metal, an unacceptable situation for a device intended to be permanently implanted in the body. Therefore, manufacturing requires a high degree of quality control and concomitant high cost.

Alternative or additional layers have also been used in stents. Applicant's U.S. Pat. No. 6,099,561 discloses a stent structure having three fundamental layers, a first underlying layer of a base metal that functions to provide high mechanical strength, a second intermediate layer that functions to provide high fluoroscopic visibility—preferably a noble metal layer or alloy thereof—, and a top layer of a particularly beneficial biocompatible material—preferably a ceramic-like material such as iridium oxide or titanium nitrate. The intermediate layer of elemental or alloy of a noble metal is uninterrupted, highly adherent for tight coverage and substantially uniform thickness. Such an intermediate layer tends to assure avoidance of a galvanic potential that would lead to corrosion of the lesser, base metal, including such a condition that may obtain with a layer of ceramic-like metal overlying the base metal at points where fissures might exist were it not for the uninterrupted presence of the intermediate noble metal layer. The 3-layer stent of the '561 patent exhibits mechanical strength, small physical dimensions, increased visibility, long-term stability, and a highly biocompatible surface that enables rapid endothelialization with low occurrence of restenosis.

The '896 application, of which the present application is a continuation-in-part, discloses a stent adapted to be expanded from a first vessel-navigable diameter to a larger second vessel-deployed diameter, which is composed of material that possesses all of the desirable attributes mentioned above and yet can be fabricated in a single homogeneous structure without need for additional layers. The stent material is niobium, preferably with a sufficient amount of zirconium added, typically less than 5% by weight, for hardness of the combination. The stent may thus be fabricated from a single piece of tubing at relatively low cost and yet with all of the desirable features of non-allergenic reaction, excellent and adequate radiopacity (density twice that of stainless steel), distortionless for MRI, highly flexible, sufficiently elastic to be plastically deformable, non-brittle, sufficient strength to resist vessel recoil, and sufficient thinness to minimize obstruction to blood flow, and highly biocompatible. The niobium/zirconium material is anodized to provide surface oxidation. This material is readily treatable by post-processing such as annealing, electro-polishing for rounded edges, and so forth.

Additional surface modification or other substances or agents may be applied to the stent surface, such as vapor deposition of even more highly biocompatible layers, to preclude occlusion from restenosis or thrombosis during the acute stage following deployment of the stent. For example, iridium and iridium oxide, titanium nitrate, or compositions such as described in U.S. Pat. No. 5,679,815, might be applied.

The stent may also be formed from a sintering process with small microspheres by heat and pressure (e.g., such as disclosed in U.S. Pat. No. 5,198,187), thereby avoiding costly production and control steps.

SUMMARY OF THE INVENTION

Applicant has found that a stent composed primarily of niobium alloyed with a trace amount (e.g., less than 5% by weight, preferably about 1%) of preferably zirconium, but alternatively tantalum or titanium, or additive material such as described in U.S. Pat. Nos. 5,472,794 and 5,679,815, exhibits considerably improved performance structurally, e.g., to avoid brittleness and thrombogenicity, if the completed stent is annealed post-fabrication in a substantially oxygen-free atmosphere. The latter should be an extreme vacuum environment of from $10^{-4}$ to $10^{-6}$ millibars (mbar) pressure, preferably $10^{-5}$ mbar or less vacuum pressure, with less than about 80 parts per million (ppm) of $O_2$, at an annealing temperature exceeding 400° C., preferably about 1200° C., for several hours, nominally more than one hour. $O_2$ and $H_2$ content of the stent material should be kept at low levels.

A surface layer of oxide, such as iridium oxide, may be applied as a post-annealing step by anodizing or sputtering, for example, to a thickness of, say, 200–300 nanometers (nm). Oxygen content of the material is kept within the specified bounds by wrapping the stent in an $O_2$-gathering tantalum foil.

BRIEF DESCRIPTION OF THE DRAWING

The above and still further aims, objectives, features, aspects and attendant advantages of the present invention will become apparent to those skilled in the art from the following detailed description of a best mode presently contemplated of practicing the invention by reference to certain preferred embodiments and methods of manufacture thereof, taken in conjunction with the sole FIGURE of drawing which shows a side view of a preferred stent structure for the invention (in which the far side is not shown for the sake of simplicity).

DETAILED DESCRIPTION OF THE BEST MODE OF PRACTICING THE INVENTION

The sole FIGURE is a perspective view (not to scale) of a stent 10 in the form of a hollow tubular self-supporting structure composed primarily of niobium (Nb), with a trace amount of zirconium (Zr), titanium (Ti) or tantalum (Ta) for example, preferably zirconium, the trace amount preferably less than 5%, more preferably approximately 1%, and remainder niobium. The added trace metal improves physical characteristics of the stent for its intended function. Typically, the stent material used by applicant also has negligible amounts of tantalum (Ta, about 180 micrograms per gram (μg/g)), iron (Fe, <20 μg/g), silicon (Si, about <μg/g), tungsten (W, <20 μg/g), nickel (Ni, <20 μg/g), molybdenum (Mo, <20 μg/g), hafnium (Hf, <20 μg/g), carbon (C, about 7 μg/g), and nitrogen (N, about 53 μg/g), as well as amounts of hydrogen (H) and oxygen (O) primarily introduced during the processing.

Important values of these minor elemental constituents are those of $O_2$ and $H_2$. Both of these elements tend to increase brittleness of the stent material dramatically if their values too high. Chemical finishing ($H_2$ source) and the vacuum annealing ($O_2$ source) steps of applicant's process are intentionally set to keep the value of H at less than 10 ppm and the value of O at less than 80 ppm to prevent brittleness, with a desire to keep the O content at less than about 35 μg/g.

The presently preferred process of fabricating the stent is performed in the following sequence of steps: (1) tube processing from Nb-1%Zr ingots; (2) laser cutting of tube; (3) mechanical and chemical finishing; (4) electropolishing; (5) vacuum annealing; and (6) anodizing or sputtering with surface coating, preferably iridium oxide. Anodizing or sputtering of iridium oxide ("Irox") before vacuum annealing will increase the $O_2$ amount in the core material, so the Irox is preferably applied after annealing and, additionally, excess oxygen content is avoided by a technique to be described presently herein.

In the laser cutting process, the tubular stent member is provided with a multiplicity of through-holes or openings 12 through sidewall 15, defined and bounded by a plurality of struts or links 13, which enables expansion of the stent diameter when the device is to be deployed at a target site in a vessel, duct or tract of the human body. The openings 12 may be precisely cut out to form a latticework sidewall using a narrow laser beam of a conventional laser that follows a programmable pattern. The removed material that formerly occupied openings 12 is discarded following the cutting.

For example, the resulting pattern in the latticework sidewall 15 is a network of interconnected struts 13 which are optimized for orientation predominantly parallel to the longitudinal axis 16 of the tube 11, with none of the struts oriented perpendicular (i.e., transverse) to the axis 16, so that no strut interconnecting any other struts in the latticework is oriented to lie completely in a plane transverse to the longitudinal axis, without running from one end of the stent to the opposite end. This type of structure, which is described in detail in applicant's U.S. Pat. No. 6,398,805, provides a relatively very low friction characteristic (or coefficient of friction) of the outer surface 17 of the stent, to ease advancement of stent 10 in a vessel, duct or tract to a site for deployment. The network or latticework of struts 13 may define a series of longitudinally repeating circumferential rows 20 of openings 12, in which each opening has a shape which resembles the outline of a handlebar moustache, or of a Dutch winged cap, with each opening bounded by alternating links in wavelets of higher and lower crests in successive rows of each circumferential column displaced along the length of the cylindrical element. If viewed upside down, the openings have a shape resembling the outline of a ram's head with horns projecting at either side upwardly from the head and then downwardly, each opening bounded by alternating links in wavelets of shallower and deeper troughs in successive rows of each circumferential column displaced along the length of the cylindrical element.

Each pair of struts such as 21, 22 bounding an opening 12 in any given row 25 are in the shape of circumferentially displaced wavelets with adjacent circumferentially aligned higher and lower crests 26, 27, respectively, in which the wavelets intersect (30) one another at one or both sides of the crests (30, 31). The intersection 30 of struts (or wavelets) at one side of the adjacent circumferentially aligned crests 26, 27 of row 25 is tangential to a crest 33 of the immediately adjacent row 35, and the intersection 31 of struts (or wavelets) at the other side of those crests is tangential to a crest 37 of the immediately adjacent row 38. Interconnecting points such as 40 between the struts may be notched to enhance symmetrical radial expansion of the stent during deployment thereof.

When the stent 10 is crimped onto a small diameter (low profile) delivery balloon (not shown), the adjacent circumferentially aligned crests of each row move closer together, and these portions will then fit into each other, as the pattern formed by the latticework of struts allows substantial nesting together of the crests and bows, which assures a relatively small circumference of the stent in the crimped condition. Such a stent is highly flexible, and is capable of undergoing bending to a small radius corresponding to radii of particularly tortuous coronary arteries encountered in some individuals, without permanent plastic deformation.

As the stent 10 is partially opened by inflation of the balloon during deployment, the adjacent crests begin to separate and the angle of division between struts begins to open. When the stent is fully expanded to its deployed diameter, the latticework of struts takes on a shape in which adjacent crests undergo wide separation, and portions of the struts take on a transverse, almost fully lateral orientation relative to the longitudinal axis of the stent. Such lateral orientation of a plurality of the struts enables each fully opened cell to contribute to the firm mechanical support offered by the stent in its fully deployed condition, to assure a rigid structure which is highly resistant to recoil of the vessel wall following stent deployment. The particular configuration of the stent structure, while highly desirable, is illustrative only.

The stent may be pre-opened after fabrication to relieve stresses. Pre-opening produces a stent inner diameter that allows the stent to slide comfortably over the uninflated mounting balloon, for ease of crimping the stent onto the balloon. Annealing may be performed after pre-opening by heating the stent structure to an appropriate temperature for a predetermined interval of time.

The niobium/zirconium material of the stent is fabricated in any conventional manner for producing alloys, with the zirconium amounting from 1% to 5% by weight, preferably about 2%, and the remainder niobium. For example, the manufacturing process may be performed by sintering particles or microspheres of the constituent metals under heat and pressure. Rather than using zirconium as the trace metal, a trace amount (e.g., one to three percent) of titanium or tantalum may be alloyed with the niobium for added strength and other desirable physical characteristics. Other suitable alternative additive materials include those described in U.S. Pat. Nos. 5,472,794 and 5,679,815, for example. The alloy is then formed into tubing and the through holes are provided in its side wall as described above.

According to the process aspect of the present invention, the principally niobium stent exhibits much improved performance structurally, with improved resistance against brittleness and thrombogenicity, by annealing the completed structure post-fabrication in a substantially oxygen-free atmosphere. Preferably, the environment is one of an extreme vacuum ranging from about $10^{-5}$ to about $10^{-6}$ millibars pressure, with less than about 80 parts per million (ppm) of $O_2$. The annealing is performed at a temperature greater then 400° C., preferably at about 1100–1200° C. for at least one hour, and more preferably for several hours.

The stent structure can be produced with a wall thickness of about 85 μm, which offers sufficient mechanical strength to resist the natural recoil of the blood vessel wall following deployment of the stent, as well as excellent visibility under fluoroscopy, but which does not obstruct the vessel lumen to any significant extent. Since it has none of the distortion encountered with metallic 316L stents to MRI, use of the niobium-based stent in noninvasive monitoring also of cerebral and peripheral vessels is highly beneficial.

The surface layer of iridium oxide is preferably applied post-annealing to avoid brittleness-producing oxygen contribution to the material. Surface modification of the stent to apply the preferred coating of iridium oxide, or alternatively, of titanium nitrate is achieved by vapor deposition, plasma deposition, or other conventional method. Such modification may be used to give the stent a rough surface. Alternatively, the surface may be anodized for oxidation of the niobium to achieve reduced immunoresponse and less thrombogenicity.

The most critical portion of the process currently utilized by applicant as the best mode for practicing that aspect of the invention is as follows:

1. Dissolve the natural oxide layer (<2 nm thick) by placing stents for more than 1 minute in 10% hydrofluoric (HF) acid.
2. Wrap Nb-1%Zr stents loosely in tantalum foil gathering $O_2$ because of its high oxygen affinity, to further prevent undesirable contribution to oxygen content.
3. Introduce wrapped stents plus additional gather foil into recipient chamber.
4. Heat up in 5 hrs. to 600° C. maintaining vacuum $<10^{-4}$ mbar (preferably $<10^{-5}$ mbar, but with recognition of considerably higher equipment cost).
5. Maintain temperature for about 2 hours.
6. Increase heating in 5 hours to 1120° C., maintaining vacuum $<10^{-4}$ mbar.
7. Maintain set temperature for another 3 hours.
8. Cool down to 60° C. while maintaining vacuum.
9. Remove stents and the $O_2$-gather foil from recipient chamber.

Although a best mode of practicing the invention has been disclosed by reference to a preferred method and embodiment, it will be apparent to those skilled in the art from a consideration of the foregoing description that variations and modifications may be made without departing from the spirit and scope of the invention. Accordingly, it is intended that the invention be limited only by the appended claims and the rules and principles of applicable law.

What is claimed is:

1. A stent formed from a single homogeneous tube composed principally of niobium with a trace of additional metal for alloy formation and reinforcement, the stent composition having an oxygen content of less than about 35 micrograms per gram of stent.

2. The stent of claim 1, wherein the trace metal is selected from a group including zirconium, tantalum and titanium, and said trace is less than approximately 5%.

3. The stent of claim 1, wherein the stent is annealed and the annealing was performed in a substantially oxygen-free vacuum environment ranging from about $10^{-4}$ to about $10^{-6}$ millibars of pressure.

4. The stent of claim 1, including an iridium oxide coating on the stent surface.

5. The stent of claim 1, including a titanium nitrate coating on the stent surface.

6. The stent of claim 1, including a niobium oxide coating on the stent surface.

* * * * *